United States Patent [19]

Adams

[11] 4,440,013

[45] Apr. 3, 1984

[54] GAS CHROMATOGRAPH, FOURIER TRANSFORM, INFRARED SPECTROSCOPY SYSTEM

[75] Inventor: Gary E. Adams, Danbury, Conn.

[73] Assignee: International Business Machines Corp., Armonk, N.Y.

[21] Appl. No.: 354,555

[22] Filed: Mar. 3, 1982

[51] Int. Cl.³ .................... G01N 21/01; G01N 31/08
[52] U.S. Cl. ................................. 73/23.1; 250/343; 356/410
[58] Field of Search ................ 73/23.1; 250/343, 344, 250/345; 356/410, 36

[56] References Cited

U.S. PATENT DOCUMENTS

| | | | |
|---|---|---|---|
| 3,444,722 | 5/1969 | Roof | 73/23.1 |
| 3,649,829 | 3/1972 | Randolf | 73/23.1 |
| 3,879,984 | 4/1975 | Welland | 73/23.1 |
| 3,920,334 | 11/1975 | Steichen et al. | 250/343 |
| 4,029,416 | 6/1977 | Hawes | 250/343 |

OTHER PUBLICATIONS

Brown et al., "Rapid Scan Infrared Spectrometer for Operation with Support Coated Tubular or Packed Column Gas Chromatographs", *Anal. Chem.*, 42 (Mar. 1971), pp. 355–358.

Crawford et al., "Organic Analysis with a Combined Capillary GS/MS/FTIS", *Anal. Chem.* 54 (Apr. 1982), pp. 817–820.

Azarraga, "Gold Coating of Glass Tubes for GC/FTIRS, Light-Pipe Gas Cells", 34 (Mar. 1980), pp. 224–225.

M. D. Erickson, "Gas Chromatography/Fourier Transform Infrared Spectroscopy Applications", App. Spectrosc. Rev. 1979, 15, 261–325.

*Primary Examiner*—Gerald Goldberg
*Assistant Examiner*—John E. Chapman, Jr.
*Attorney, Agent, or Firm*—Douglas R. McKechnie

[57] ABSTRACT

A gas chromatograph Fourier transform infrared (GC/FTIR) system includes a GC oven having a flexible capillary column therein for separating components of a sample. The column discharges effluent directly into a light pipe associated with an FTIR spectroscope. An auxiliary flow of carrier gas is added to the effluent at the light pipe to convey constituents through the light pipe free from tailing or peak broadening.

12 Claims, 4 Drawing Figures

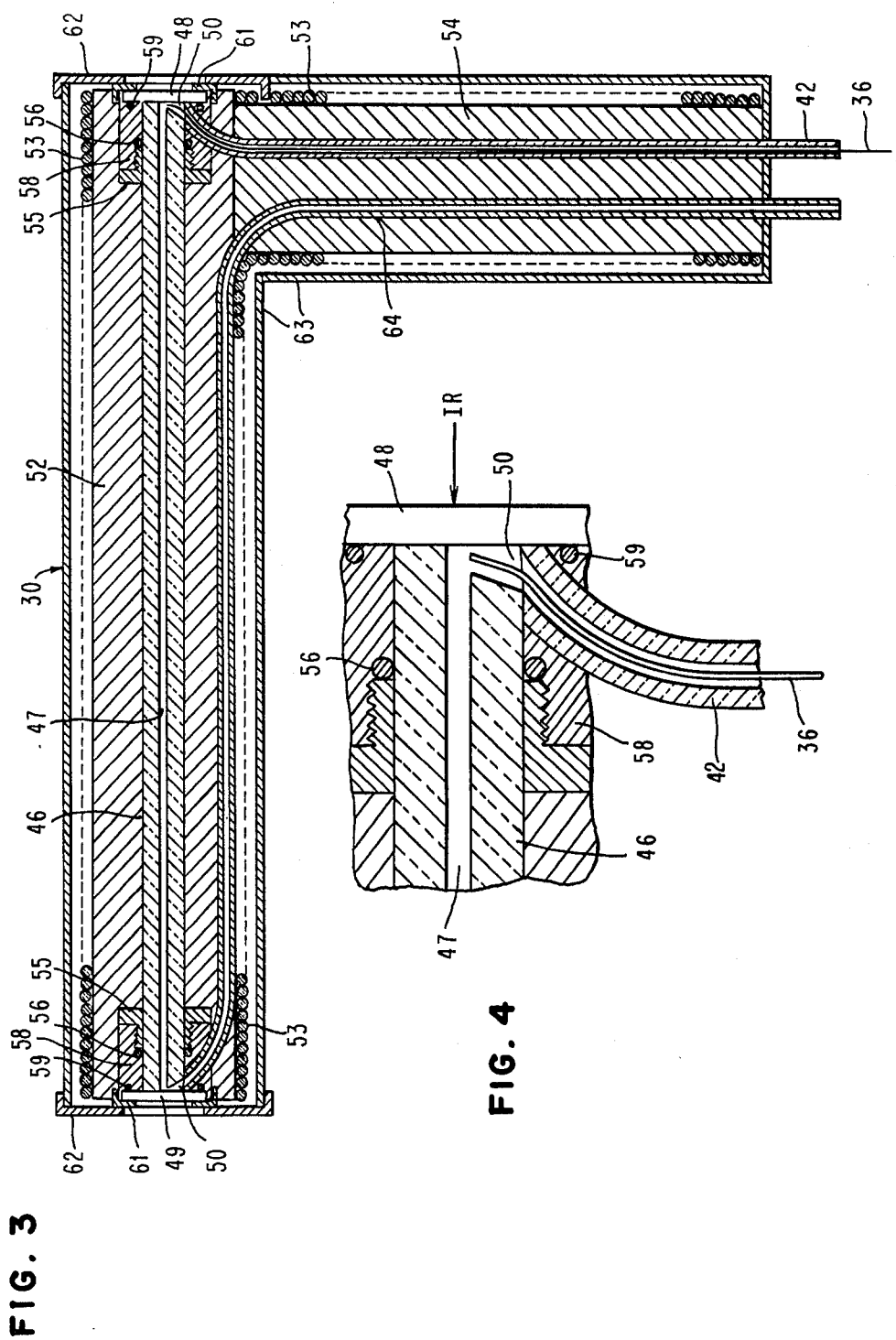

GAS CHROMATOGRAPH, FOURIER TRANSFORM, INFRARED SPECTROSCOPY SYSTEM

FIELD OF THE INVENTION

This invention relates to improvements in Gas Chromatograph (GC), Fourier Transform (FT) Infra-Red (IR) Spectroscopy Systems and, more particularly, to improvements in apparatus for separating gaseous constituents of a sample in a GC and passing the resultant effluent continuously through a FTIR light pipe for detection and analysis.

BACKGROUND OF THE INVENTION

The combination of GC and FTIR Analytical Techniques is well known whereby a sample is separated into its constituents in a GC. An FTIR Spectroscope and data system detects and analyzes the constituents in a rapid and highly sensitive manner. GC/FTIR systems generally comprise a GC including an oven containing a separating column. A carrier gas continuously flows through the column and a sample, generally in liquid form, is injected into the GC and vaporized so that its constituents are picked up by the carrier gas and separated, by partitioning, as they flow through the column. The effluent from the column is passed through a light pipe whereby the various constituents or peaks thereof flow at different times through the light pipe. Infrared energy from an interferometer is directed through the light pipe and is absorbed by the constituents in a manner indicative of the quantity and type of constituent. The IR energy is detected so as to create an electrical signal or interferogram which is then digitized and inputed into a data processing system. The interferogram is then subjected to a Fourier transform and other mathamatical computations to provide the desired analysis and output.

In prior art GC/FTIR systems, the separating column is located within an oven and the light pipe is located external to the oven. A transfer tube is connected to the exit end of the separating column and to the input end of the light pipe. Various fittings are used at the different connections and it becomes a difficult problem to achieve a laminar gas flow from a column, through the transfer tube and the light pipe. Some of the fittings may introduce turbulence and eddy currents and possibly be so shaped as to create dead volumes. The net result is that peak broadening and tailing might occur that affect the resolution of the system. This problem becomes more acute when the column is a capillary column having a relatively long length in relationship to its inner diameter. The capillary column inner diameter is generally small and it might differ from the inner diameter of the transfer tube and light pipe so that the problem further occurs of maintaining the constituents in a separated or resolved state.

In order to produce spectra wherein spectral band differences are well defined, a high signal-to-noise ratio is desired. Such results could be obtained by having a highly concentrated sample component in the IR light pipe or IR sample beam. Heretofore, this was accomplished by using a relatively wide bore GC column, which could contain a large amount of sample in the column and therefore provide the higher concentration to achieve the high signal-to-noise ratio. However, wide bore columns generally provided low resolution and poor separation efficiency.

SUMMARY OF THE INVENTION

The present invention relates to high resolution gas chromotography using very narrow bore capillary GC columns to efficiently separate very complex samples with a high degree of resolution. The use of a very narrow bore GC column yields very highly resolved components which emerge as extremely sharp, well defined peaks flowing from the end of the column. Even though the sample quantity per component is extremely low, the peaks are so sharp and concentrated when measured by the amount of time it takes for a peak to go past a particular point (measured in tenths of a second) that a high signal-to-noise ratio can be obtained doing multiple rapid scans on a sensitive FTIR spectrometer. The problem then becomes one of transferring a very narrow component peak from the narrow bore GC column to the light pipe broadening the peak and destroying its high concentration in time. Conventional transfer methods either greatly broaden the peak or lose it altogether through diffusion or other causes.

Accordingly, one of the objects of the invention is to provide a high resolution GC/FTIR system using a narrow bore capillary column, with means to transfer very narrow component peaks from the GC column to the light pipe in order to achieve high resolution and a high signal-to-noise ratio.

Another object of the invention is to provide a GC/FTIR interface allowing a conventional GC to be combined with a conventional FTIR spectrometer.

A further object of the invention is to provide a GC/FTIR system in which a very narrow bore capillary column is connected to one end of a light pipe so as to completely eliminate any problem that might otherwise be caused by the use of transfer tubes.

A further object is to provide a way to connect a narrow bore GC column to a light pipe so that effluent from the column emerges directly into an IR beam passing through the light pipe.

Another object of the invention is to provide a GC/FTIR system in which very narrow peaks from a narrow bore capillary GC column flow rapidly through a light pipe with very little loss of resolution.

Briefly, the manner in which these and other objects and advantages of the invention are obtained is to provide a GC/FTIR system in which a narrow bore capillary column is mounted within a GC oven. The exit end of the column terminates at one end of the light pipe whereby effluent flowing from the column emerges directly in the path of the IR beam passing through the light pipe. A secondary flow of gas is introduced at the connection between the column and light pipe so as to rapidly carry any peaks, constituents or components emerging from the column, through the light pipe.

Other objects and advantages of the invention will be apparent from the following description taken in connection with the accompanying drawings wherein:

FIG. 3 is a longitudinal sectional view through the light pipe assembly shown schematically in FIG. 2;

FIG. 4 is an enlarged detail view of a portion shown in FIG. 3.

DETAILED DESCRIPTION

Figure 1:
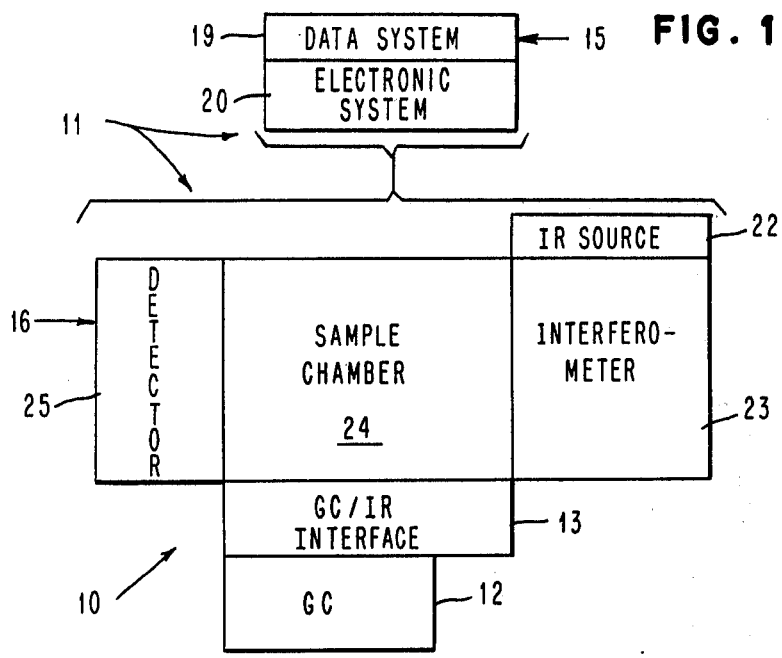
FIG. 1 is a block diagram of a GC/FTIR system embodying the invention.

Referring now to the drawings, FIG. 1 illustrates a GC/FTIR system 10 embodying the invention. This system generally comprises an FTIR Spectrometer 11, a GC 12, and a GC/IR Interface 13. Spectrometer 11 and GC 12 are conventional or commercially available items which are modified, in the manner described below, to be combined with the novel interface 13.

Spectrometer 11 may be one of the IR/90 or IR/80 series of FTIR Spectrometers available from IBM Instruments, Inc. Such spectrometer generally comprises a console 15 an optic bench 16. Console 15 houses a data system 19 and an electronic system 20 which control the operation of the spectrometer and analyze the data during the course of operation of the system. Optic bench 16 comprises an IR source 22 that directs IR energy into an interferometer 23. Optic bench 16 further comprises a sample chamber 24 and IR detector 25. Spectrometer 11 is operable in either a conventional mode or in a GC mode. In the conventional mode, IR energy from the interferometer is transmitted through or reflected from a sample placed in sample chamber 24, the flow of energy being directed by a series of mirrors or lenses through the system. The energy from the sample is then directed into detector 25. In the course of operation, the interferometer 23 includes a movable mirror (not shown) which reciprocates back and forth and produces interference within the IR energy so that during each scan or movement of the mirror, the output of detector 25 produces an interferogram. This output is an electrical signal in analog form that is then amplified and digitized in the electronic system and fed into the data system 19 where it undergoes a Fourier transform and is analyzed.

Figure 2:
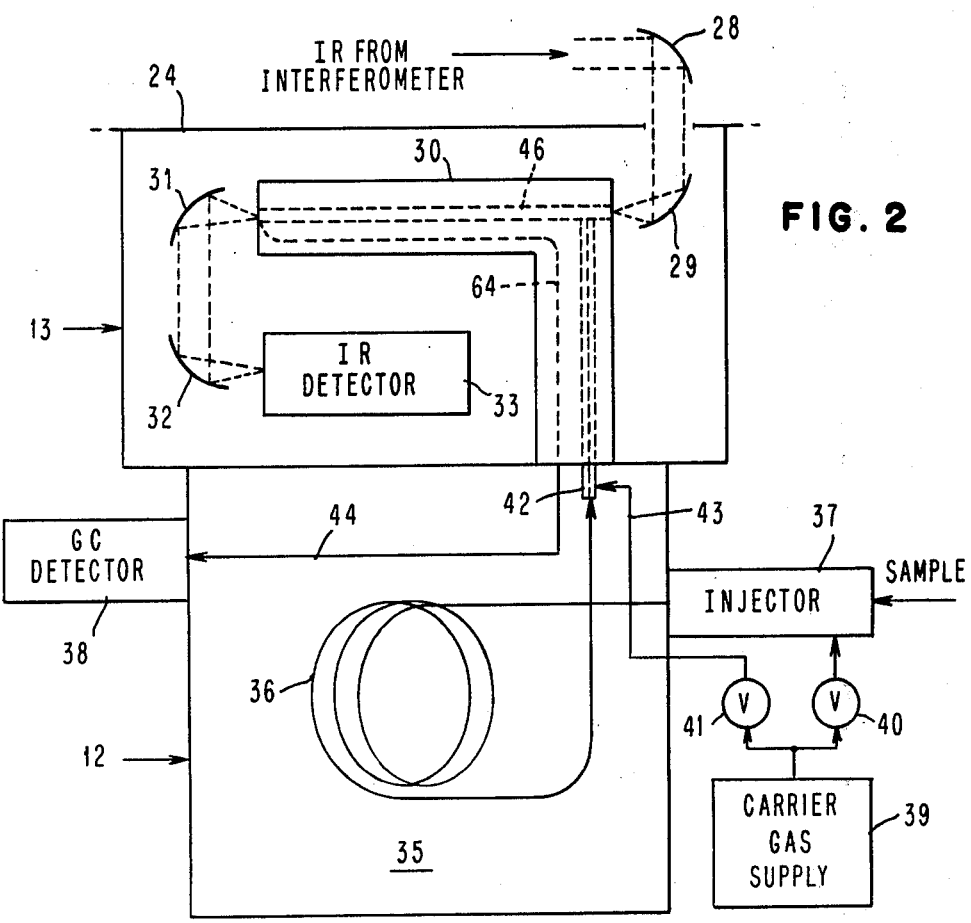
FIG. 2 is a schematic diagram of a portion of the system shown in FIG. 1.

In the GC mode of operation one of the mirrors in sample chamber 24 is replaced, as shown in FIG. 2, by a reflecting lens 28 that directs the IR energy through an opening in sample chamber 24 and interface 13 onto another mirror 29 which focuses the energy and directs it into one end of a light pipe assembly 30. The energy emerging from assembly 30 is directed by mirrors 31 and 32 into an IR detector 33. The details of light pipe assembly 30 are shown more fully in FIGS. 3 and 4 and will be discussed below.

With reference to FIG. 2, GC 12 includes an oven 35 in which is located a continuous, one-piece, flexible, narrow bore capillary column 36 of fused silica. One end of the column is connected to an injector 37 which receives a sample and carrier gas from a supply 39. A valve 40 permits a flow rate of the carrier gas to be adjusted or regulated. The other end of column 36 passes through a glass lined tube 42 whereby the effluent from the column is admitted into the interior of light pipe assembly 30. A second valve 41 is connected to a line 43 for controlling the flow of an auxiliary supply of a carrier gas into tube 42. Another line 44 receives gas passing from the light pipe assembly 30 and directs it into a GC detector 38 so that this detector can be used in addition to IR detector 33. Thus, GC 12 comprises an conventional type of GC which has been modified by the addition of a valve 41, auxiliary flow line 43, return line 44 and a hole to accommodate tube 42.

Light pipe assembly 30 includes a glass light pipe or tube 46 having a central bore 47 coated with gold to reflect IR energy traversing through bore 47. A flat window 48 transparent to IR energy, abuts one end of tube 46 so as to close off one end of bore 47 and thereby cause gas admitted into the end of the light pipe to flow along bore 47. As best seen in FIG. 4, the upper end of tube 42 abuts one end of tube 46 and window 48. A radial passage 50 communicates between the interior of tube 42 and bore 47 to provide a flow passage for auxiliary carrier gas. The end of column 36 passes through tube 42 and extends into passage 50 whereby effluent emerging from column 36 discharges directly into bore 47 into the path of IR energy being transmitted through the bore. Obviously, to allow the flow of the auxiliary gas, the inner diameter of tube 42 is greater than the outer diameter of capillary column 36. Additionally, the end of tube 42 is suitably sealed at light pipe 46 to prevent the leakage of gas.

Light pipe 46 extends through an aluminum heat transfer block 52 around which is wrapped a thermostated heater coil 53. A second aluminum heat transfer tube 54 extends at right angles to tube 52 and is encircled by heater 53. At each end, light pipe 46 is connected into block 52 by means of a compression nut 55. A high temperature O-ring 56 is held between nut 55 and a fitting 58 and sealed around the side of tube 46. A second O-ring 59 abuts between the ends of fitting 58 and window 48. A window retaining ring 61 is screwed onto the end of fitting 58 for holding the window in place against the tube and sealing O-ring 59 against window 48. The assembly is completed by means of two end caps 62 fitted onto the exterior of a stainless steel outer casing 63. A return line 64 extends from another radial flow passage at the exit end of light pipe 46, through blocks 52 and 54 and is connected to the return line 44 in GC 12.

During operation of the system, the various heaters are energized to bring the desired operating parts to the proper temperatures. This operation includes adjusting heater 53 so that the temperature in tube 42, light pipe 46 and the enclosed end of column 36 is sufficiently high to prevent the condensation of any gas therein. Valve 40 is adjusted to provide the desired flow rate of carrier gas. When a sample is injected or placed in injector 37, it is vaporized and caught up by the carrier gas. As the sample in the carrier gas passes through column 36, the sample is separated by the partitioning process into various constituents. While gas is flowing through the GC, the FTIR spectrometer 11 is operated and the mirror scan is set at a rate that is related to the desired resolution and flow of a component of the sample through light pipe 46. The scan rate should be such that at least one scan occurs during the time it takes any single constituent to move through light pipe 46. This is accomplished by setting the flow rate of the auxiliary gas supply 41 to be such that when a constituent emerges from the end of column 36 into bore 47, the auxiliary carrier gas pushes the constituent through the light pipe as a "slug", in a highly concentrated form, so as to provide a high signal-to-noise ratio in the energy detected by detector 33. After the constituents flow through light pipe 46, they flow through a line 64 and then may either be exhausted or fed via line 44 to GC detector 38 for further analysis.

One of the primary advantages of the invention stems from the flexibility of the fused silica column 36. Such a column is normally furnished in coiled, circular form and because of flexibility of the material, one end of the column can be threaded or inserted through tube 42 to terminate within the light pipe. Another advantage is that the column empties directly into the light pipe bore without any intermediate transfer tube or additional fitting which could create dead volumes, introduce turbulence or otherwise cause a peak broadening or tailing.

In an illustrative or exemplary embodiment of the invention, fused silica capillary columns are commercially available having I.D.'s ranging from 0.25 to 0.4 mm and O.D.'s ranging from 0.35 to 0.6 mm. Tube 42 has an I.D. of 0.7 mm to accomodate any one of such sized columns. Light pipe 46 has a length of 36 cm and an I.D. of 1.4 mm. A typical flow rate for the effluent from column 36 is 1 cc/min and the flow rate for the auxiliary gas could be adjusted in the range of 5 to 15 cc/min to provide peaks free from or with a minimal amount of broadening. The system has a sensitivity of being capable of detecting at least as low as 10 nanograms of ethyl acetate.

While I have illustrated and described the preferred embodiment of my invention, it is to be understood that I do not limit myself to the precise construction herein disclosed and the right is reserved to all changes and modifications coming within the scope of the invention as defined in the appended claims.

Having thus described my invention, what I claim as new, and desire to secure by Letters Patent is:

1. In a GC-IR system for analyzing the constituents of a sample, which system comprises a gas chromatograph including an injector and an oven, and an IR spectrometer for irradiating said constituents, with IR energy, the combination comprising:
   a light pipe having an elongated bore coated to direct IR energy from said spectrometer along said bore and through any constituents therein,
   and a high-resolution capillary narrow-bore GC column for separating said sample into constituents, said column being at least substantially disposed in said oven and having one end connected to said injector and another end disposed at one end of said bore for discharging effluent from said column directly into said bore into the path of said IR energy, whereby constituents are continuously separated by said column up to the point of discharge whereupon such constituents are immediately irradiated with said IR energy.

2. The combination of claim 1 wherein:
   said light pipe is located external to and spaced from said oven, and said column is flexible and is coiled in said oven and has a substantially straight end portion that extends through a wall of said oven to said light pipe.

3. The combination of claim 2 comprising:
   a tube surrounding said end portion and having an internal diameter greater than the outer diameter of said column to define a flow passage,
   and means for introducing a carrier gas into one end of said tube whereby such gas flows from the other end of said tube into said light pipe for carrying constituents through said bore and thereby minimizing peak broadening of constituents flowing from said column through said bore.

4. The combination of claim 3 comprising:
   means for heating said tube, said end portion of said column and said light pipe to prevent condensation of any gas therein.

5. In a GC-IR system for analyzing a sample, comprising a gas chromatograph for separating said sample into constituents, and an IR spectrometer for analyzing said constituents by irradiation thereof with IR energy, the combination comprising:
   a light pipe having an elongated bore coated to reflect IR energy along said bore, a continuous one-piece capillary GC column in said gas chromatograph for separating said sample into constituents, said column terminating at said bore so that effluent from one end thereof passes directly into said bore and into the path of IR energy therein, said column being effective to continuously separate said constituents up to the point of flowing from said column into said bore, and gas flow means arranged to introduce an additional flow of gas into said effluent as said effluent emerges from said column so as to rapidly convey any constituents in said effluent through said bore without concomitant peak broadening.

6. The combination of claim 5 wherein:
   said light pipe is cylindrical and has a radial passage intersecting one end of said bore, and said one end of said column terminates at the intersection of said passage and said bore.

7. In a GC/FTIR system for analyzing a sample, comprising a gas chromatograph for separating said sample into constituents and having an injector for introducing said sample into a carrier gas, a GC column at least substantially disposed in said oven and connected at one end to said injector, and an FTIR spectrometer for irradiating said constituents with IR energy and providing an output indication of said constituents, the improvement comprising:
   an elongated light pipe having a bore extending therethrough coated to reflect IR energy through said bore,
   said column being a coiled, narrow bore, elongated, high resolution capillary column connected at one end to said injector for receiving said sample and carrier gas from said injector and continuously separating said sample along the entire length of said column into constituents which flow from the other end of said column at time spaced intervals,
   and means for mounting said other end of said column at one end of said bore of said light pipe whereby said constituents separated by said column discharge directly from said column into said bore and are immediately irradiated by IR energy passing therethrough.

8. The combination of claim 7 wherein:
   said FTIR spectrometer includes an interferometer having a scan rate sufficient to complete at least one scan for each constituent passing through said bore of said light pipe.

9. The combination of claim 7 wherein:
   said light pipe is located externally of said oven, said column is flexible and of fused silica, and said mounting means comprises a substantially straight tube extending through a wall of said oven and terminating at said one end of said bore, said tube having a bore through which said other end of said column extends.

10. The combination of claim 9 including heating means surrounding said tube and said light pipe for heating thereof to a temperature sufficient to prevent condensation of any of said constituents.

11. The combination of claim 9 comprising:
    means for supplying a second carrier gas to one end of said bore of said tube and discharging such gas at the other end thereof at such a rate as to convey constituents through said light pipe without peak broadening.

12. The combination of claim 11 wherein:
    said light pipe has a radial flow passage at said one end of said bore of said light pipe, said other end of said tube terminating at said flow passage and said other end of said column terminates in said flow passage at said bore of said light pipe.

* * * * *